(12) United States Patent
Boffo et al.

(10) Patent No.: US 11,327,062 B2
(45) Date of Patent: May 10, 2022

(54) DEVICE FOR EXAMINING AN ATMOSPHERE AND USE OF THE DEVICE

(71) Applicant: Bilfinger Noell GmbH, Wuerzburg (DE)

(72) Inventors: Cristian Boffo, Batavia, IL (US); Tatjana Pfeuffer, Wuerzburg (DE)

(73) Assignee: Bilfinger Noell GmbH, Würzburg (DE)

( * ) Notice: Subject to any disclaimer, the term of this patent is extended or adjusted under 35 U.S.C. 154(b) by 0 days.

(21) Appl. No.: 16/955,946

(22) PCT Filed: Dec. 19, 2018

(86) PCT No.: PCT/EP2018/085872
§ 371 (c)(1),
(2) Date: Jun. 19, 2020

(87) PCT Pub. No.: WO2019/121936
PCT Pub. Date: Jun. 27, 2019

(65) Prior Publication Data
US 2020/0326319 A1    Oct. 15, 2020

(30) Foreign Application Priority Data

Dec. 20, 2017    (DE) ............... 10 2017 130 755.9

(51) Int. Cl.
G01N 33/00    (2006.01)
F25B 9/14    (2006.01)
F25D 19/00    (2006.01)

(52) U.S. Cl.
CPC ......... *G01N 33/0016* (2013.01); *F25B 9/145* (2013.01); *F25D 19/006* (2013.01)

(58) Field of Classification Search
CPC .... F25B 9/145; F25D 19/006; G01N 33/0016
See application file for complete search history.

(56) References Cited

U.S. PATENT DOCUMENTS

| 5,647,228 A | 7/1997 | Sager et al. |
| 2007/0051116 A1 | 3/2007 | Glemot et al. |
| 2014/0202174 A1* | 7/2014 | Wang .................. F25B 9/14 62/6 |

(Continued)

FOREIGN PATENT DOCUMENTS

| DE | 287098 A5 | 2/1991 |
| DE | 102004037173 B3 | 12/2005 |
| JP | 201796710 A | 6/2017 |

OTHER PUBLICATIONS

Lerner et al., "An improved, automated whole air sampler and gas chromatography mass spectrometry analysis system for volatile organic compounds in the atmosphere", Atmospheric Measurement Techniques Discussions, 2016, vol. 10, pp. 291-313.

(Continued)

*Primary Examiner* — Francis C Gray
(74) *Attorney, Agent, or Firm* — The Webb Law Firm

(57) ABSTRACT

The invention relates to a device for examining an atmosphere, comprising an atmosphere analysis chamber and a cryocooler, which is thermally coupled to the atmosphere analysis chamber for cooling the atmosphere analysis chamber. The invention further relates to the use of the device for examining an atmosphere, in particular the composition of an atmosphere.

14 Claims, 2 Drawing Sheets

(56) References Cited

U.S. PATENT DOCUMENTS

| | | | | |
|---|---|---|---|---|
| 2014/0245757 A1* | 9/2014 | Garside | ............... | F25B 49/00 |
| | | | | 62/56 |
| 2015/0300719 A1* | 10/2015 | Strickland | ............. | F28D 7/106 |
| | | | | 62/62 |
| 2016/0377230 A1 | 12/2016 | Chuard et al. | | |
| 2017/0069476 A1* | 3/2017 | Takeda | ............... | G01N 15/00 |
| 2017/0168121 A1* | 6/2017 | Yu | ..................... | F25D 19/006 |
| 2017/0323764 A1* | 11/2017 | Muto | .................. | H01J 27/26 |
| 2019/0170621 A1* | 6/2019 | Doherty | ............... | F17C 3/085 |

OTHER PUBLICATIONS

Ross, Jr. "Aerospace Coolers: a 50-Year Quest for Long-life Cryogenic Cooling in Space", Cryogenic Engineering Fifty Years of Progress, 2006, pp. 225-284.

Ross, Jr. "Refrigeration Systems for Achieving Cryogenic Temperatures", Chapter 6 of Low Temperature Materials and Mechanisms, CRC Press, Boca Raton, FL., 2016, pp. 109-181.

* cited by examiner

DEVICE FOR EXAMINING AN ATMOSPHERE AND USE OF THE DEVICE

CROSS-REFERENCE TO RELATED APPLICATIONS

This application is the United States national phase of International Application No. PCT/EP2018/085872 filed Dec. 19, 2018, and claims priority to German Patent Application No. 10 2017 130 755.9 filed Dec. 20, 2017, the disclosures of which are hereby incorporated by reference in their entirety.

BACKGROUND OF THE INVENTION

Field of the Invention

The invention relates to a device for examining an atmosphere and a use of the device.

Examinations of the composition of the atmosphere and the interaction of its components (e.g. aerosols and impurities) with one another are an important part of current climate research.

Description of the Related Art

There are devices for examining the atmosphere with an atmosphere analysis chamber. It has tuned out that a reliable, effective and as low-maintenance as possible cooling of the atmosphere analysis chamber is important for the use of such devices. Devices with cooling circuits, in which a coolant circulates through pipes, heat exchangers and cooling unit, have proven to be quite costly and maintenance-intensive and are therefore not well suited for field use. The same applies to systems that use a tempering gas.

On this basis, the present invention has the object of providing a device for examining the atmosphere which functions more reliably, more effectively and preferably requiring less maintenance.

SUMMARY OF THE INVENTION

According to the invention, this object is achieved by a device for examining an atmosphere comprising an atmosphere analysis chamber and a cryocooler which is thermally coupled to the atmosphere analysis chamber for cooling the atmosphere analysis chamber. In particular, the cryocooler may be coupled to a region of the wall forming the atmosphere analysis chamber.

A space-saving and low-maintenance cooling of the atmosphere analysis chamber is achieved through the use of a cryocooler to cool the atmosphere analysis chamber instead of a cooling circuit. Furthermore, a high cooling capacity and good temperature control are possible with a cryocooler. A cryocooler also allows a significantly extended operating temperature range, even below −200° C.

The atmosphere can be a natural atmosphere, in particular the Earth's natural atmosphere, or an artificial atmosphere.

The cryocooler may be a Gifford-McMahon cryocooler, a pulse tube cryocooler or a Stirling cryocooler. The cryocooler can be a single or multi-staged cryocooler, but preferably a single-staged one The object is further achieved by using the device described above for examining an atmosphere, especially the composition of an atmosphere.

Various embodiments which apply to both the device and its use are described below. Furthermore, the embodiments can also be combined with one another.

In one embodiment, the atmosphere analysis chamber has an inlet. The atmosphere to be examined can be fed into the atmosphere analysis chamber in this way.

In a further embodiment, the atmosphere analysis chamber has two inlets, in particular arranged on opposite sides of the atmosphere analysis chamber. In this way, the atmosphere to be examined can be passed through the atmosphere analysis chamber.

In one embodiment, the cryocooler has a cooling head thermally coupled to the atmosphere analysis chamber. The cryocooler may also have several cooling heads thermally coupled to the atmosphere analysis chamber. Furthermore, several cryocoolers can also be provided, which or, respectively, whose cooling heads are thermally coupled to the atmosphere analysis chamber.

In one embodiment, the device has an outer chamber, which is preferably closed, surrounding the atmosphere analysis chamber. For example, the outer chamber can be arranged in a ring-like manner around the atmosphere analysis chamber. By providing such an outer chamber, the atmosphere analysis chamber can, at least in some regions, be thermally isolated from the environment.

In one embodiment, the outer chamber is under negative pressure, in particular vacuum. This improves the thermal insulation effect of the outer chamber.

In one embodiment, the atmosphere analysis chamber and the outer chamber are formed by an inner container and an outer container surrounding it. The wall of the inner container preferably forms the atmosphere analysis chamber or its wall, respectively. The wall of the inner container and the wall of the outer container together preferably form the outer chamber or its wall, respectively.

In one embodiment, the cooling head of the cryocooler is located inside the outer chamber. In this way, the cooling head of the cryocooler is also thermally insulated from the environment, which improves the cooling efficiency.

In one embodiment, the cooling head of the cryocooler is thermally coupled to the atmosphere analysis chamber by means of one or more thermally conductive connections. The one or more thermally conductive connections are preferably arranged inside the outer chamber. In this way the cooling efficiency is further improved.

For a more effective and more uniform cooling of the atmosphere analysis chamber, in particular several thermally conductive connections may be provided between the cooling head and different points of the atmosphere chamber, in particular different points of the wall forming the atmosphere chamber.

Flexible connections and/or connections made of a material with good thermal conductivity such as copper or aluminium are particularly suitable as thermally conductive connections. For instance, the one or more connections can be formed by one or more copper or aluminium cable wires.

In one embodiment, the wall of the atmosphere analysis chamber and/or the outer chamber is made of stainless steel, aluminium or copper.

In one embodiment, the wall of the atmosphere analysis chamber has a coating on the inner side and/or on the outer side. In this way, a better and more uniform distribution of the temperature can be achieved at the atmosphere analysis chamber. For this purpose, the coating preferably consists of a material with good thermal conductivity, for example copper.

In one embodiment, one or more heating elements are attached or thermally coupled to the atmosphere analysis chamber. The temperature of the atmosphere analysis chamber can be better regulated in this way. The one or more heating elements may, for example, be coupled or attached to one or more wall regions of the atmosphere chamber. Preferably one or more resistive heating elements are used.

In one embodiment, one or more heating elements are attached or thermally coupled to the cooling head and/or to one or more thermally conductive connections of the cooling head to one or more wall regions of the atmosphere analysis chamber. In this way, an additional heat load can be activated for the cooling head or the connections, respectively, which can support the temperature control process. The one or more heating elements are preferably resistive.

In one embodiment, a shield is provided inside the outer chamber to reduce thermal radiation between a wall region of the outer chamber and a wall region of the atmosphere analysis chamber. In this way, the heat load by radiation on the wall of the atmosphere analysis chamber can be controlled and reduced. The shield is preferably configured such that it at least partially reflects thermal radiation coming from the outside of the outer chamber. For this purpose, the shield may in particular have a multi-layer insulation.

In one embodiment, the shield is thermally coupled to a cryocooler for cooling. The cryocooler can be a cryocooler for cooling the atmosphere analysis chamber or a separate cryocooler. The cryocooler coupled to the shield is preferably configured to cool the shield to a predefined temperature range. In this way, the thermal radiation can be better shielded from the atmosphere analysis chamber.

In a further embodiment, reflective multilayer insulation can be applied directly to the outer wall of the atmosphere analysis chamber to reduce the input of radiant heat.

In one embodiment, a sensor or analytical apparatus for analysing the atmosphere is arranged in or connected to the atmosphere analysis chamber. In this way, the atmosphere entering the atmosphere analysis chamber can be analysed, especially in relation to its composition. Other measuring instruments may also be located at or in the inlet flow of the atmosphere analysis chamber or its outflow.

The measuring instruments used are preferably suitable for measuring and recording pressure conditions and/or temperatures in the atmosphere analysis chamber. Furthermore, measuring devices such as particle counters, preferably optical, or mass spectrometers for small particles may be attached to the atmosphere analysis chamber. Other advantageous measuring instruments include gas analysis devices and interferometric spectrometers from various wavelength ranges.

BRIEF DESCRIPTION OF THE DRAWINGS

Further features and advantages of the device and its use are described in the following embodiments, wherein reference is made to the enclosed drawing.

In the Drawing

FIG. 1 shows a device for examining an atmosphere with an atmosphere analysis chamber with a cooling-circuit cooling system in schematic sectional view.

Figure 1:
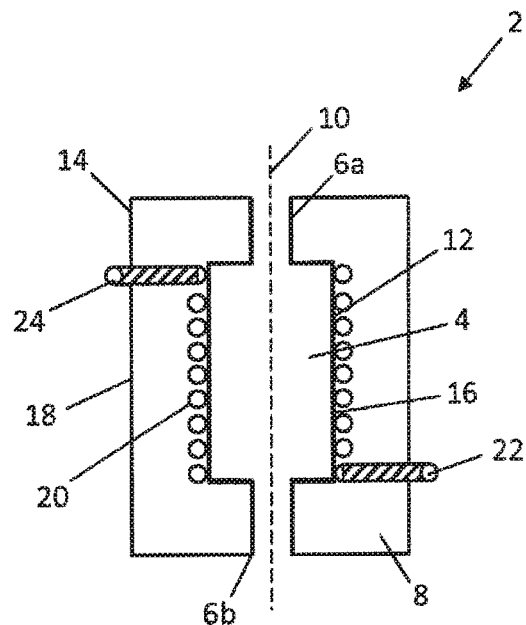
FIG. 1 shows a first device with a cooling-circuit cooling system.

Device 2 comprises an atmosphere analysis chamber 4 with two opposite inlets 6a-b and a closed outer chamber 8 surrounding them. In this case, atmosphere analysis chamber 4 and the outer chamber 8 are rotationally symmetrical to axis 10, which runs through the two inlets 6a-b.

Atmosphere analysis chamber 4 and outer chamber 8 of the device are formed by an inner container 12 and an outer container 14 surrounding it Wall 16 of inner container 12 forms the wall of atmosphere analysis chamber 4. Wall 16 also forms the wall of outer chamber 8 together with wall 18 of outer container 14.

DESCRIPTION OF THE INVENTION

To cool the atmosphere analysis chamber 4, a pipe coil 20 is mounted on the inner container 12, through which a cooling liquid flows during operation. To this end, a coolant feed line 22 and a coolant return line 24 are provided, via which the pipe coil 20 is embedded in a cooling circuit.

Figure 2:
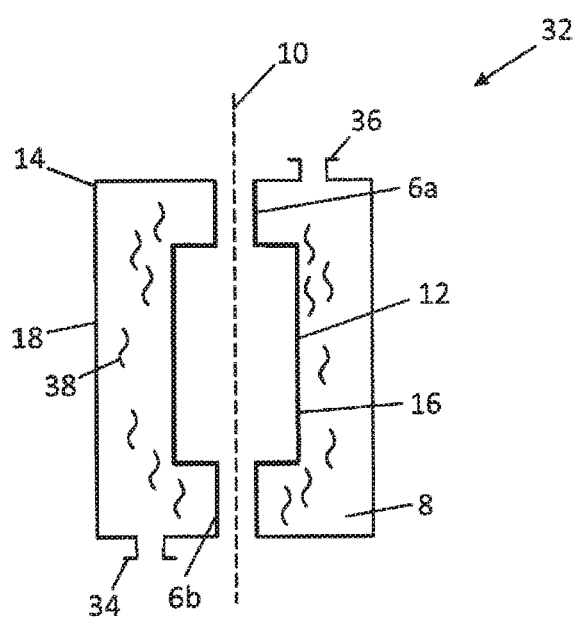
FIG. 2 shows a second device with a cooling-circuit cooling system.

FIG. 2 shows a second device for examining an atmosphere with an atmosphere analysis chamber with a cooling-circuit cooling system in schematic sectional view.

Device 32 has a similar structure to device 2. Components that correspond to one another are marked with the same reference signs.

Device 32 differs from device 2 in that cooling for the atmosphere analysis chamber 4 is provided by a tempering gas from a cooling circuit instead of the pipe coil 20 through which cooling liquid can flow.

To this end, an inlet 34 and an outlet 36 for a tempering gas of a cooling circuit are provided on the outer container. During operation, a cooled tempering gas 38 is fed through inlet 34 into the outer chamber 8 which, after flowing through the outer chamber 8, exits outer chamber 8 through outlet 36 again. The tempering gas cools wall 16 of inner container 12 and thus the atmosphere analysis chamber 4.

Devices 2 and 32 allow cooling of the atmosphere analysis chamber 4. However, cooling by means of a cooling circuit using cooling liquid as in device 2 or tempering gas as in device 32 has proven to be quite complex and maintenance-intensive.

Figure 3:
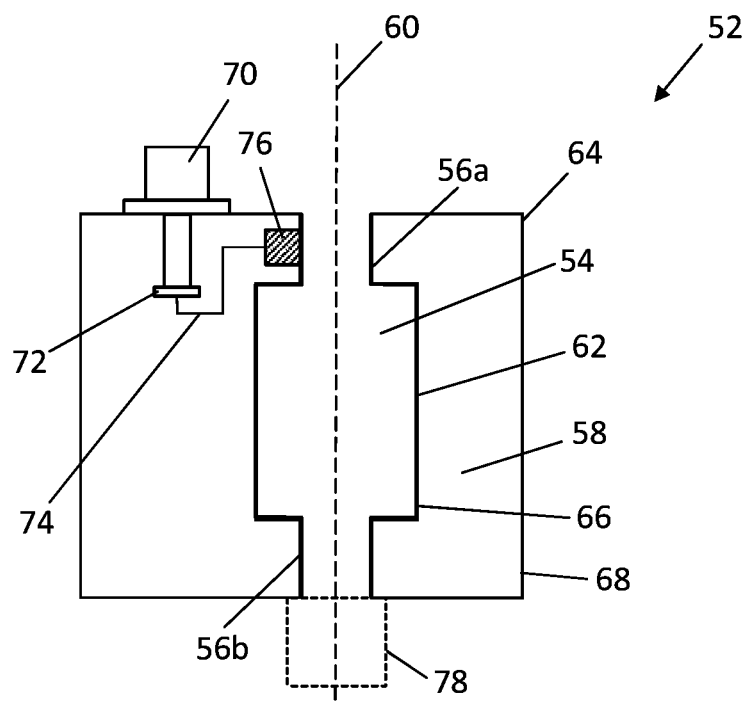
FIG. 3 shows a first embodiment of the device with a cryocooler.

FIG. 3 now shows a first embodiment of the device with a cryocooler in schematic sectional view.

Device 52 comprises an atmosphere analysis chamber 54 with two opposite inlets 56a-b and a closed outer chamber 58 surrounding it, which is under negative pressure, preferably under vacuum. Atmosphere analysis chamber 54 and outer chamber 58 are rotationally symmetrical to axis 60, which runs through the two inlets 56a-b.

Atmosphere analysis chamber 54 and outer chamber 8 of the device 52 are formed by an inner container 62 and an outer container 64 surrounding it Wall 66 of the inner container 62 forms the wall of atmosphere analysis chamber 54. Wall 66 also forms the wall of outer chamber 58 together with wall 68 of outer container 64.

A cryocooler 70 is provided to cool atmosphere analysis chamber 54. Cryocooler 70 can be a Gifford-McMahon cryocooler, a pulse tube cryocooler or a Stirling cryocooler. The cryocooler is preferably single-staged. The cryocooler has a cooling head 72, which is located in the outer chamber 58. Cooling head 72 is thermally coupled to the wall 66 via a thermally conductive connection 74 by means of a thermal link 76 and thus to the atmosphere analysis chamber 54. The thermally conductive connection 74 can, for example, be a copper cable wire or copper wire meshwork. The thermal connection 76 can be a screw connection, a solder connection or a clamp connection. In FIG. 3, cooling head 72 is connected to wall 66 in the region of the inlet 56a. Wall 66 has a copper coating on the inside (i.e. on the side located inside the atmosphere analysis chamber 54) and/or on the outside (i.e. on the side located in the outer chamber 58), which results in a more even tempering of atmosphere analysis chamber 54.

Figure 4:
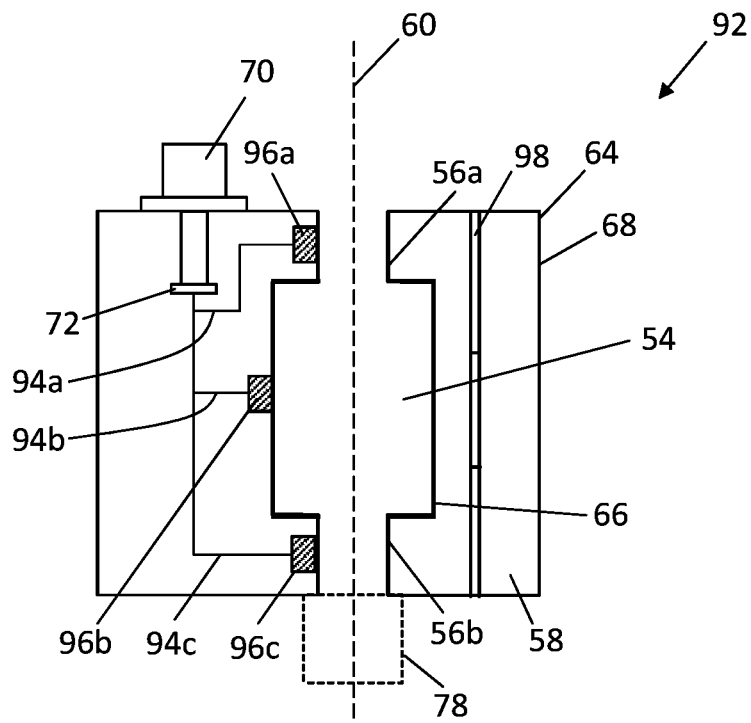
FIG. 4 shows a second embodiment of the device with a cryocooler.

FIG. 4 shows a second embodiment of the device with a cryocooler in schematic sectional view.

Device 92 has a similar structure to device 52. Components that correspond to one another are marked with the same reference signs.

Device 92 differs from device 52 in that cooling head 72 is thermally coupled via several thermally conductive connections 94a-c by means of respective thermal connections 96a-c to wall 66 and thus to the atmosphere analysis chamber 54. In FIG. 4, cooling head 72 is connected to wall 66 in the region of inlet 56a, in the region of inlet 56b and in a region lying in-between.

Within outer chamber 58, between wall 66 of inner container 62 and wall 68 of outer container 64, there is a shield 98 arranged that reduces the transmission of thermal radiation from wall 68 to wall 66. For an even more effective reduction of thermal radiation transfer, shield 98 can be thermally connected to cooling head 72.

One or more controllable heating elements may be provided on cooling head 72, on the thermally conductive connections 94a-c and/or on wall 66, which heating elements allow better control and/or regulation of the temperature of atmosphere analysis chamber 54.

It has been found that the use of a cryocooler 70 enables low-maintenance and efficient cooling of atmosphere analysis chamber 54. Particularly efficient cooling can be achieved with the configurations according to devices 52 and 92. A measuring instrument 78 may be used for measuring and recording pressure conditions and/or temperatures in the devices 52 and 92.

The invention claimed is:

1. A device for examining an atmosphere comprising:
   an atmosphere analysis chamber; and
   a cryocooler which is thermally coupled to the atmosphere analysis chamber in order to cool the atmosphere analysis chamber,
   characterised in that
   an optical particle counter is attached to the atmosphere analysis chamber.

2. The device according to claim 1, characterised in that the atmosphere analysis chamber has two inlets in particular arranged on opposite sides of the atmosphere analysis chamber.

3. The device according to claim 1, characterised in that the cryocooler has a cooling head which is thermally coupled to the atmosphere analysis chamber.

4. The device according to claim 1, characterised in that the device has a preferably closed outer chamber surrounding the atmosphere analysis chamber.

5. The device according to claim 4, characterised in that the outer chamber is under negative pressure.

6. The device according to claim 4, characterised in that the cooling head of the cryocooler is arranged inside the outer chamber.

7. The device according to claim 3, characterised in that the cooling head of the cryocooler is thermally coupled to the atmosphere analysis chamber by means of one or more thermally conductive connections, wherein the one or more thermally conductive connections are preferably arranged within the outer chamber.

8. The device according to claim 1, characterised in that the wall of the atmosphere analysis chamber and/or the wall of the outer chamber is made of stainless steel, aluminium or copper.

9. The device according to claim 1, characterised in that the wall of the atmosphere analysis chamber has a coating on the inner side and/or on the outer side.

10. The device according to claim 1, characterised in that one or more heating elements are affixed or thermally coupled to the atmosphere analysis chamber.

11. The device according to claim 3, characterised in that one or more heating elements are affixed or thermally coupled to the cooling head.

12. The device according to claim 4, characterised in that a shield is provided inside the outer chamber to reduce thermal radiation between a wall region of the outer chamber and a wall region of the atmosphere analysis chamber.

13. The device according to claim 12, characterised in that the shield is thermally coupled to a cryocooler for its cooling.

14. The device according to claim 1, characterised in that a sensor or analytical apparatus for analysing the atmosphere is arranged in or connected to the atmosphere analysis chamber.

* * * * *